United States Patent

Berneth et al.

[11] Patent Number: 5,328,994
[45] Date of Patent: Jul. 12, 1994

[54] AZINONEUTROMETHINES

[75] Inventors: Horst Berneth, Leverkusen; Karin Hassenrück, Düsseldorf, both of Fed. Rep. of Germany

[73] Assignee: Bayer Aktiengesellschaft, Leverkusen, Fed. Rep. of Germany

[21] Appl. No.: 19,503

[22] Filed: Feb. 19, 1993

[30] Foreign Application Priority Data

Feb. 25, 1992 [DE] Fed. Rep. of Germany ........ 4205632

[51] Int. Cl.$^5$ .................. C09B 29/048; C09B 69/06
[52] U.S. Cl. .................. 534/607; 534/795; 534/770; 534/788; 534/753; 534/775; 548/141; 548/161; 548/198; 548/206; 548/264.8; 548/331.5; 546/143; 546/209
[58] Field of Search ........... 534/607, 795, 753, 770, 534/775, 788

[56] References Cited

U.S. PATENT DOCUMENTS

| | | | |
|---|---|---|---|
| 3,673,169 | 6/1972 | Weaver et al. | 534/795 |
| 4,994,563 | 2/1991 | Walter et al. | 534/728 |
| 5,208,325 | 5/1993 | Berneth et al. | 534/607 |

OTHER PUBLICATIONS

J. Chem. Soc., Chem. Commun., 1990, pp. 325 and 326.
Dyes and Pigments 16, 1991, pp. 183 to 196.

*Primary Examiner*—Floyd D. Higel
*Assistant Examiner*—MarySusan H. Gabilan
*Attorney, Agent, or Firm*—Sprung Horn Kramer & Woods

[57] ABSTRACT

New azinoneutromethines of the formula

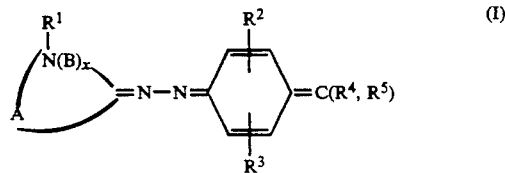

in which the symbols used have the meaning given in the description, a process for their preparation and their use in thermal and photochromic recording materials, as nonlinear optical materials, as photoconductors in electrophotography and for dyeing fibres and woven fabrics of polyester and plastics.

4 Claims, No Drawings

AZINONEUTROMETHINES

The present invention relates to new azinoneutromethines, a process for their preparation and their use. Azinoneutromethines of the formula (I)

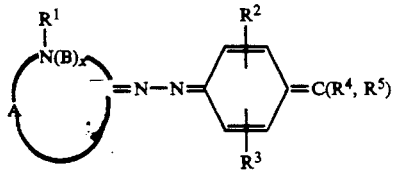

in which

R$^1$ represents C$_1$- to C$_{22}$-alkyl, C$_4$- to C$_{10}$-cycloalkyl, C$_7$- to C$_{14}$-aralkyl, C$_6$- to C$_{10}$-aryl, or a heterocyclic radical which is optionally bonded via C$_1$- to C$_2$-alkylene and contains 1 to 4 nitrogen, oxygen and/or sulphur atoms and 4 to 12 C atoms, it being possible for all these radicals optionally to be substituted, R$^2$ and R$^3$ independently of one another represent hydrogen, halogen, hydroxyl, cyano, C$_1$- to C$_8$-alkyl, C$_1$- to C$_8$-alkoxy, C$_4$- to C$_{10}$-cycloalkoxy, C$_7$- to C$_{14}$-aralkyloxy or C$_1$- to C$_{20}$-acylamino, R$^4$ and R$^5$ independently of one another represent cyano, C$_1$- to C$_8$-alkoxycarbonyl, C$_4$- to C$_7$-cycloalkoxycarbonyl, C$_6$- to C$_{10}$-aryloxycarbonyl, aminocarbonyl, mono-C$_1$- to C$_8$-alkylaminocarbonyl, di-C$_1$- to C$_8$-alkylaminocarbonyl, C$_6$- to C$_{10}$-arylaminocarbonyl, aminocarbonyl which is substituted by heterocyclic radicals which contain 5 to 7 atoms and contain N, S and/or O, or phenyl which is substituted by cyano and/or nitro, or R$^4$ and R$^5$, together with the C atom in between, represent a ring which contains 5 or 6 atoms, optionally contains up to 2 nitrogen and/or oxygen atoms and is optionally substituted by cyano, halogen, C$_1$- to C$_4$-alkyl or C$_6$- to C$_{10}$-aryl, A complements the ring in which it is located to form a 5- to 7-membered aromatic or quasiaromatic ring which is optionally benzo- or naphtho-fused, optionally contains a further nitrogen, oxygen or sulphur atom, and is optionally substituted by cyano, nitro, C$_1$- to C$_4$-alkyl, C$_7$- to C$_{12}$-aralkyl, C$_6$- to C$_{10}$-aryl, C$_1$- to C$_4$-alkoxy, a 5- to 6- membered ring which is optionally bonded via C$_1$- to C$_2$-alkylene and contains up to 2 N, S and/or O atoms, C$_1$- to C$_4$-alkylthio, C$_6$- to C$_{10}$-arylthio, amino, mono- or di-C$_1$- to C$_8$-alkylamino, C$_4$- to C$_8$-cycloalkyl-C$_1$- to C$_4$-alkylamino, C$_7$- to C$_{12}$-aryl-C$_1$- to C$_4$-alkylamino, mono- or di-C$_6$- to C$_{10}$-arylamino, pyrrolidino, piperidino, morpholino or C$_1$- to C$_6$-acylamino, B represents CR$^B$=CH, where R$^B$=hydrogen or C$_1$- to C$_6$-alkyl, and x represents zero or 1, have now been found.

Preferred azinoneutromethines of the formula (i) are those in which the radical

R$^2$ is in the ortho-position relative to the

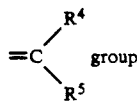

and

R$^3$ is in the ortho-position relative to the =N-N= group and in the para-position relative to R$^2$, and represents C$_1$- to C$_{22}$-alkyl which is optionally branched and/or substituted by a total of up to three substituents from the group comprising C$_1$- to C$_4$-alkoxy, fluorine, chlorine, bromine, hydroxyl, cyano and aminocarbonyl, cyclopentyl, cyclohexyl, benzyl, phenethyl, phenyl which is optionally substituted by a total of up to 2 substituents from the group comprising C$_1$- to C$_4$-alkyl, C$_1$- to C$_4$-alkoxy, chlorine and cyano, or pyridylethyl, R$^2$ represents C$_1$- to C$_4$-alkyl, C$_1$- to C$_4$-alkoxy, chlorine, bromine, hydroxyl or cyano, R$^3$ represents hydrogen, C$_1$- to C$_4$-alkyl, C$_1$- to C$_4$-alkoxy, chlorine, bromine, hydroxyl, cyano, C$_1$- to C$_{20}$-alkanoylamino which is optionally substituted by up to nine fluorine atoms, or benzoylamino which is optionally substituted by a total of up to two substituents from the group comprising methyl, methoxy and chlorine, R$^4$ represents cyano, C$_1$- to C$_4$-alkoxycarbonyl, cyclopentoxycarbonyl, cyclohexoxycarbonyl, phenoxycarbonyl, aminocarbonyl, mono- or di-C$_1$- to C$_4$-alkylaminocarbonyl, anilinocarbonyl or nitrophenyl, R$^5$ represents cyano, A complements the ring in which it is located to form a pyrazole, imidazole, triazole, thiazole, thiadiazole, benzimidazole, benzothiazole, pyridine, pyrazine, pyrimidine or quinoline ring, it being possible for these rings optionally to be substituted by a total of up to two substituents from the group comprising chlorine, cyano, phenyl, C$_1$- to C$_4$-alkyl, C$_1$- to C$_4$-alkoxy, C$_1$- to C$_4$-alkylthio, phenylthio, di-C$_1$- to C$_4$-alkylamino, cyclohexyl-C$_1$- to C$_4$-alkylamino, benzyl-C$_1$- to C$_4$-alkylamino, phenylamino, phenyl-C$_1$- to C$_4$-alkylamino, pyrrolidino, piperidino or morpholino, it being possible for the substituents C$_1$- to C$_4$-alkoxy, C$_1$- to C$_4$-alkylthio, di-C$_1$- to C$_4$-alkylamino and cyclohexyl-C$_1$- to C$_4$-alkylamino in turn optionally to contain a total of up to two substituents from the group comprising chlorine, methoxy, ethoxy, hydroxyl and cyano, and for the substituents phenylamino and phenyl-C$_1$- to C$_4$-alkylamino in turn optionally to contain a total of up to two substituents from the group comprising methyl, methoxy, cyano and chlorine, and B represents CH=CH and x represents zero or 1.

Particularly preferred azinoneutromethines of the formula (I) are those in which the radical R$^2$ is in the ortho-position relative to the

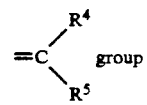

and

R$^3$ is in the ortho-position relative to the =N-N= group and in the para-position relative to R$^2$, and R$^1$ represents C$_1$- to C$_{16}$-alkyl which is optionally branched and/or substituted by a chlorine, cyano or methoxy group, or represents benzyl, R$^2$ represents methyl, ethyl, methoxy, ethoxy or chlorine, R$^3$ represents hydrogen, methyl, ethyl, methoxy, ethoxy, chlorine, cyano, formylamino, acetylamino, propionylamino, butyroylamino, octanoylamino, stearoylamino, trifluoroacetylamino, nonafluorobutyroylamino, benzoylamino, methylbenzoylamino or chlorobenzoylamino, $R^4$ represents cyano, methoxycarbonyl, ethoxycarbonyl, amidocarbonyl or 4-nitrophenyl, $R^5$ represents cyano, A complements the ring in which it is located to form one of the rings (II) to (VI)

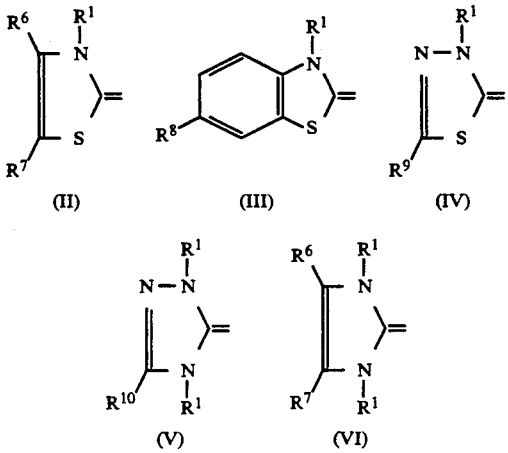

(II)  (III)  (IV)

(V)  (VI)

in which $R^1$ has the abovementioned meaning, $R^6$ represents hydrogen, methyl, ethyl, n-propyl, i-propyl, tert-butyl or phenyl and $R^7$ represents hydrogen, methyl, ethyl, chlorine or bromine, or $R^6$ and $R^7$ together represent $-(CH_2)_4-$, $R^8$ represents hydrogen, methyl, methoxy or chlorine, $R^9$ represents hydrogen, methyl, ethyl, phenyl, methylthio, phenylthio, anilino, 4-methylanilino, 4-methoxyanilino, N-methylanilino, dimethylamino, diethylamnino, dipropylamino, dibutylamino, dihydroxyethytamino, dihydroxypropylamino, hydroxyethylcyclohexylamino, pyrrolidino, piperidino or morpholino and $R^{10}$ represents hydrogen, methyl, ethyl, phenyl or hydroxypropyl, and x represents zero.

In especially preferred azinoneutromethines of the formula (I), $R^2$ represents methoxy and $R^4$ represents cyano, and the other symbols have the meaning and position mentioned as particularly preferred.

A process has also been found for the preparation of azinoneutromethines of the formula (I), which is characterised in that a compound of the formula (VII)

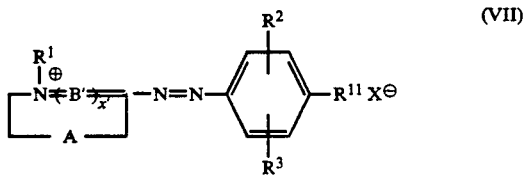

(VII)

in which $R^1$, $R^2$, $R^3$ and A have the meaning given in the case of formula (I), B' represents $CR^{B'}$-CH, where $R^{B'}$ = hydrogen or $C_1$- to $C_6$-alkyl, x' represents zero or 1, $R^{11}$ represents halogen, alkoxy, phenoxy, monoalkylamino, dialkylamino, N-cycloalkyl-N-alkylamino or N-aralkyl-N-alkytamino and $X^\ominus$ represents an anion, is reacted with a methylene-active compound of the formula (VIII)

(VIII)

in which $R^4$ and $R^5$ have the meaning given in the case of formula (I).

In formula (VII), $R^{11}$ preferably represents chlorine, $C_1$- to $C_4$-alkoxy, phenoxy, mono-$C_1$- to $C_4$-alkylamino, di-$C_1$- to $C_4$-alkylamino, N-$C_5$- to $C_7$-cycloalkyl-N-$C_1$- to $C_4$-alkylamino or N-phenyl-N-$C_1$- to $C_4$-alkylamino, and $X^{63}$ preferably represents chloride, bromide, hydrogen sulphate, ½ an equivalent of sulphate, methosulphate, dihydrogen phosphate, ½ an equivalent of hydrogen phosphate, trichlorozincate, tetrafluoborate or perchlorate.

In the formulae (VII) and (VIII), $R^1$ to $R^5$ and A preferably and particularly preferably have the meaning mentioned as preferred or particularly preferred in the case of formula (I), and B' preferably denotes CH-CH, and x' preferably denotes zero or 1, particularly preferably zero.

The compounds of the formula (VII) and their preparation are known (see, for example, German Patent Specification 1,044,023, Belgian Patent Specification 825,455, French Patent Specification 1,145,751, German Offenlegungsschrift 2,819,197, U.S. Pat. No. 3,051,697, French Patent Specification 1,462,723, French Patent Specification 1,378,853 and German Offenlegungsschrift 2,811,258), or they can be prepared in a manner analogous to known preparations.

The compounds of the formula (VIII) are known reagents.

The preparation process according to the invention is preferably carried out in a solvent, preferably in the presence of a base, and, for example, at temperatures between 0° C. and the boiling point of the particular reaction mixture.

Suitable solvents are, for example, water, alcohols, such as methanol, ethanol, n-propanol, i-propanol, butanol, methoxyethanol and methoxypropanol, chlorinated hydrocarbons, such as chloroform and 1,2-dichloroethane, carboxylic acids, such as acetic acid, and dipolar solvents, such as acetonitrile, dimethylformamide, N-methylpyrrolidone, dimethyl sulphoxide and tetraethylurea, as well as any desired mixtures of these solvents.

Suitable bases are, for example, alkali metal hydroxides and oxides and alkaline earth metal hydroxides and oxides, such as sodium hydroxide, potassium hydroxide, calcium hydroxide and magnesium hydroxide, alkali metal carbonates and bicarbonates and alkaline earth metal carbonates and bicarbonates, such as sodium carbonate, sodium bicarbonate, potassium carbonate and calcium carbonate, alcoholates, such as sodium methylate, sodium ethylate and potassium tert-butylate, and amines, such as triethylamine, triethanolamine, triisopropanolamine and N,N-dimethylaniline, and salts of carboxylic acids, such as sodium acetate and potassium acetate.

It is possible to employ, for example, an equimolar amount of base or an excess of base, based on the particular compound of the formula (VII).

Preferred reaction temperatures are those between 15° and 50° C.

It has also been found that the azinoneutromethines of the formula (I) can be used as dyestuffs in thermal and photochromic recording media, as nonlinear optical materials and as photoconductors in electrophotography. These possible uses can be realised, for example, as follows:

Thermal recording materials can be divided into two categories. In one case, the dyestuff is transferred as such and gives a coloured marking. In the second case, a colourless form of the dyestuff is converted into a coloured form by the action of heat.

Examples of the first case are dyestuff diffusion and dyestuff sublimation transfer printing processes. In these, a dyestuff which diffuses or sublimes readily is incorporated into a layer on a thin carrier material, for example of polyester. When this colour-donating layer is brought into contact with a receiving layer, which is also on a carrier material, the dyestuff from the colour-donating layer can be transferred to the receiving layer by a thermal print head controlled by electrical signals, and forms a pattern on the receiving layer corresponding to the electrical signals. Such a recording medium is described, for example, in European Published Specification 384,040.

The azinoneutromethine dyestuffs according to the invention can be incorporated into such a colour-donating layer with solvents. They are distinguished by good sublimation properties. Suitable solvents for this use are, for example, ethers, such as tetrahydrofuran, chlorinated hydrocarbons, such as chloroform, 1,2-dichloroethane and chlorobenzene, esters, such as ethyl acetate and butyl acetate, and dipolar solvents, such as acetonitrile, dimethylformamide, N-methylpyrrolidone, dimethyl sulphoxide and tetramethylurea, and mixtures thereof.

In the second case, the azinoneutromethine dyestuffs according to the invention can be applied, for example, as a deeply coloured solution in a solvent, for example in one of the abovementioned solvents, to a substrate. If the solvent is allowed to vaporise, for example by evaporation or in vacuo, the coating becomes decolourised. It is then colourless or only slightly coloured. Under the action of heat, an intensive coloration, which is stable, develops again.

Photochromic recording materials can comprise a dyestuff or a colourless derivative of a dyestuff on a carrier material of, for example, plastic. They can also be applied as Langmuir-Blodgett films to a carrier material. image-wise exposure of this coating leads to a change in colour or colour development, which can be used for optical data recordings. Such materials are described, for example, in European Published Specifications 193,931 and 391,631.

The colourless or only slightly coloured layer which azinoneutromethines according to the invention give, after removal of the solvent, on application of their solutions to a substrate, spontaneously becomes intensely coloured, with a colour which is stable for a prolonged period of time, under the action of light. Azinoneutromethines according to the invention can therefore be used as a constituent of photochromic recording materials.

Nonlinear optical materials have a dielectric susceptibility of the second order which depends on the field strength and can result in a number of dispersive effects. Thus, for example, doubling the frequency allows generation of light of half the wavelength, compared with the incident light. The electrooptical effect allows a change in the refractive index when an electric field is applied. The frequency mixing and the frequency division allow continuous adjustment of laser light. On the basis of these effects, nonlinear optical materials can be used, for example, as electrooptical switches, for frequency and intensity control of laser light, and for holography, information processing and integrated optics. Such uses are described, for example, by D. Lupo et al. in Adv. Materials 3, 54 (1991) and in German Offenlegungsschrift 3,743,833.

The azinoneutromethines according to the invention display emission of light of half the wavelength when exposed to laser light. They are therefore nonlinear optical materials.

Photoconductor drums which contain organic dyestuffs and pigments as photoconductors are employed in electrophotography. In this, a layer of a suitable photoconductive dyestuff or pigment in a binder of plastic is applied to a metallic carrier material. A layer of a charge-conducting substance in an organic binder is applied on top. The drum is charged up to a few hundred volts by means of a corona discharge. Image-wise exposure of the charged drum allows the charge to drain at the exposed areas. The drum which has been charged image-wise in this manner now attracts oppositely charged toner powder and transfers this image-wise to a sheet of paper. Such a system is described, for example, by D. M. Burland and L. B. Schein in Physics Today 1986, 46.

As photoconductor dyestuffs, the azinoneutromethines according to the invention lead initially to high charging and then to good discharge under exposure in such an electrophotographic process.

Azinoneutromethines of the formula (I) are also suitable for dyeing fibres and woven fabrics of polyester and plastics, for example polystyrene, polycarbonate and acrylonitrile/butadiene/styrene copolymers.

EXAMPLES

Example 1 a) 167 g of 2-amino-5-diisopropylamino-1,3,4-thiadiazole were diazotised with 272 g of 42% strength by weight nitrosylsulphuric acid in a mixture of 400 ml of glacial acetic acid, 120 g of 48% strength by weight aqueous sulphuric acid and 40 g of 85% strength by weight aqueous phosphoric acid at −5° C. The resulting solution was added dropwise to a solution of 156 g of 4-acetaminoveratrol in 400 ml of glacial acetic acid. After 1 hour, 263 g of sodium acetate were added, and the dyestuff which had precipitated was filtered off with suction and dried. 294 g of a red powder of the formula (IX)

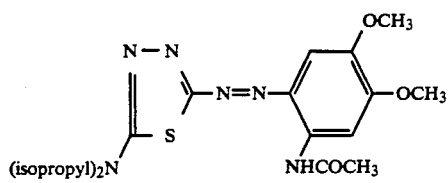

resulted.

b) 20.3 g of the dyestuff thus obtained were stirred in 100 ml of glacial acetic acid with 20 g of butyl bromide at 70° C. for 5 hours. The mixture was then diluted with 500 ml of waiter and clarified with active charcoal, and 30 g of sodium chloride and finally 25 ml of 2 molar aqueous zinc chloride solution were added. The dyestuff which had precipitated was filtered off with suction and dried. 22.6 g of a violet powder of the formula (X)

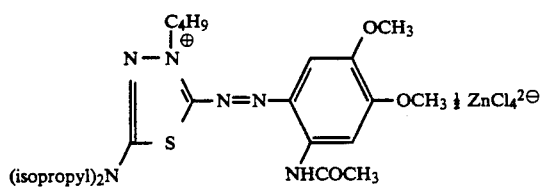

resulted.

c) 11.3 g of this dyestuff were initially introduced into 160 ml of methanol, together with 1.45 g of malodinitrile. Thereafter, 4.24 g of sodium carbonate were slowly sprinkled in at room temperature. A thick precipitate separated out, and was filtered off with suction and washed thoroughly with methanol and water. After drying, 7.2 g (73% of theory) of platelets having a greenish shimmer and a melting point of 233° C. were obtained. The product corresponded to the formula (XI)

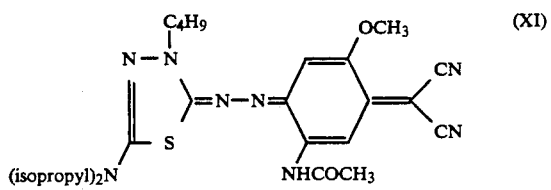

The $\lambda_{max}$ value of (XI) in dimethylformamide was 640 nm.

Example 2

730 mg of malodinitrile and 2.1 g of sodium carbonate were added to 4.2 g of a compound of the formula (XII)

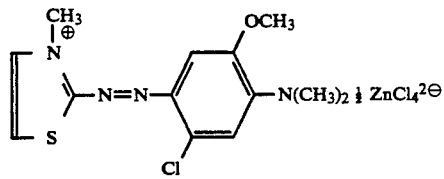

in 50 ml of methanol. After 2 hours, the precipitate was filtered off with suction and washed thoroughly with methanol and water. After drying, 2.3 g (70% of theory) of the compound of the formula (XIII) were obtained in the form of violet platelets

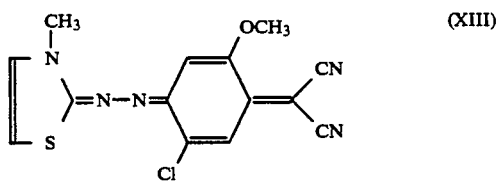

The following $\lambda_{max}$ values were determined for the compound of the formula (XIII): 632 nm in dimethylformamide and 608 nm in chloroform. The IR spectrum had a characteristic band at 2200 cm$^{-1}$.

Example 3 to 26

The following dyestuffs of the formula (XIV) were obtained analogously to Example 1c or 2, starting from the corresponding cationic dyestuffs

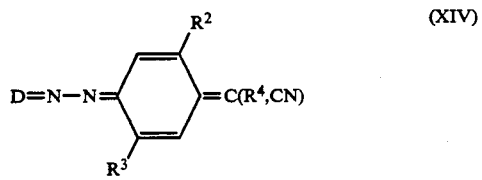

TABLE

| Example No. | D | $R^1$ | $R^2$ | $R^3$ | $R^4$ | analogous to Example | $\lambda_{max}$ in DMF (nm) |
|---|---|---|---|---|---|---|---|
| 3 |  | $CH_3$ | $OCH_3$ | $NHCOCH_3$ | $CN$ | 1c | 607 |
| 4 | 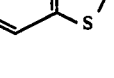 | $CH_3$ | $OCH_3$ | $Cl$ | $CN$ | 2 | 688 |

TABLE-continued

| Example No. | D | R[1] | R[2] | R[3] | R[4] | analogous to Example | $\lambda_{max}$ in DMF (nm) |
|---|---|---|---|---|---|---|---|
| 5 | N–N(R[1])–C(=)(S)–C=C–N(isopropyl)$_2$ | CH$_3$ | OCH$_3$ | OCH$_3$ | CN | 2 | 636 |
| 6 | N–N(R[1])–C(=)(S)–C=C–N(isopropyl)$_2$ | CH$_3$ | OCH$_3$ | CH$_3$ | CN | 2 | 662 |
| 7 | N–N(R[1])–C(=)(S)–C=C–N(isopropyl)$_2$ | CH$_3$ | OCH$_3$ | NHCOCH$_3$ | CN | 2 | 642 |
| 8 | N–N(R[1])–C(=)(S)–C=C–N(isopropyl)$_2$ | CH$_3$ | OCH$_3$ | NHCOCH$_3$ | COOC$_2$H$_5$ | 1c | 602 |
| 9 | N–N(R[1])–C(=)(S)–C=C–N(isopropyl)$_2$ | CH$_3$ | OCH$_3$ | H | CN | 2 | 675 |
| 10 | N–N(R[1])–C(=)(S)–C=C–N(isopropyl)$_2$ | CH$_3$ | CH$_3$ | NHCOCH$_3$ | CN | 2 | 654 |
| 11 | N–N(R[1])–C(=)(S)–C=C–N(isopropyl)$_2$ | CH$_3$ | Cl | NHCOCH$_3$ | CN | 2 | 650 |
| 12 | benzothiazoline (N(R[1]), S) | CH$_3$ | CH$_3$ | CH$_3$ | CN | 2 | 603 |

TABLE-continued

| Example No. | D | R$^1$ | R$^2$ | R$^3$ | R$^4$ | analogous to Example | $\lambda_{max}$ in DMF (nm) |
|---|---|---|---|---|---|---|---|
| 13 | piperidine-substituted thiazole with N—N, R$^1$ | CH(CH$_3$)$_2$ | OCH$_2$C$_6$H$_5$ | NHCOCH$_3$ | COOC$_8$H$_{17}$ | 2 | 600 |
| 14 | N-methyl-N-phenyl thiazole with N—N, R$^1$ | C$_4$H$_9$ | OCH$_3$ | NHCOC$_6$H$_5$ | p-NO$_2$—C$_6$H$_4$ | 1c | |
| 15 | C$_6$H$_5$-substituted thiazole, R$^1$ | C$_8$H$_{17}$ | OC$_6$H$_5$ | CH$_3$ | CN | 2 | 610 |
| 16 | 6-chlorobenzothiazole, R$^1$ | C$_{16}$H$_{33}$ | OCH$_3$ | NHCOCF$_3$ | CN | 1c | 600 |
| 17 | 4,5,6,7-tetrahydrobenzothiazole, R$^1$ | C$_2$H$_5$ | CH$_3$ | CH$_3$ | COOCH$_3$ | 2 | 580 |
| 18 | 4-methylthiazole with N—N, R$^1$ | CH$_3$ | OC$_2$H$_5$ | CH$_3$ | COONHC$_2$H$_5$ | 2 | |
| 19 | 4-(phenylthio)thiazole with N—N, R$^1$ | CH$_3$ | C$_2$H$_5$ | Cl | CN | 2 | |
| 20 | quinoline, R$^1$—N | C$_4$H$_9$ | OCH$_3$ | H | COOCH$_3$ | 2 | |

TABLE-continued

| Example No. | D | $R^1$ | $R^2$ | $R^3$ | $R^4$ | analogous to Example | $\lambda_{max}$ in DMF (nm) |
|---|---|---|---|---|---|---|---|
| 21 | (1-methyl-pyrazol-3-yl with $R^1$ on N) | $CH_3$ | $OCH_3$ | H | CN | 1c | |
| 22 | (thiazole with $R^1$-N, and $(CH_3-CH(OH)-CH_2)_2N$– substituent) | $CH_3$ | $OC_2H_5$ | $NHCOC_{15}H_{31}$ | CN | 1c | 639 |
| 23 | (thiazole with $R^1$-N, and $(CH_3)_2N$– substituent) | $C_{16}H_{33}$ | $OCH_3$ | $NHCOCH_3$ | CN | 1c | 640 |
| 24 | (1-methyl-pyrazol-3-yl with $R^1$ on N) | $CH_3$ | $OCH_3$ | $NHCOCH_3$ | CN | 1c | 575 |
| 25 | (thiazole with $R^1$-N, and N(cyclohexyl)(HOC$_2$H$_4$) substituent) | $CH_3$ | $OCH_3$ | $NHCOC_2H_5$ | CN | 1c | 638 |
| 26 | ($R^1$-N-S-C(CH$_3$)= ring) | $CH_3$ | $OC_2H_5$ | H | CN | 2 | |

Example 27 to 29

The following dyestuffs of the formula (I) were obtained analogously to Example 1c or 2, starting from the corresponding cationic dyestuffs:

Example 27

In the resulting dyestuff of the formula (I), A complemented the ring in which it is located to form

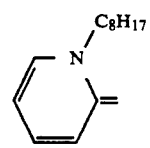

$R^2$ represented $OCH_3$, $R^3$ represented hydrogen and $R^4$ and $R^5$ represented $COOC_2H_5$. The procedure was analogous to Example 2.

Example 28

In the resulting dyestuff of the formula (I), A complemented the ring in which it is located to form

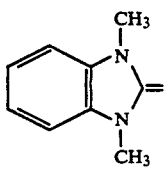

$R^2$ and $R^3$ represented $OCH_3$ and $R^4$ and $R^5$ together represented the radical

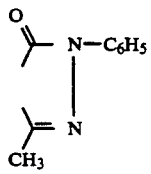

The procedure was analogous to Example 2.

Example 29

In the resulting dyestuff of the formula (I), A complemented the ring in which it is located form

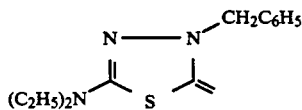

$R^2$ represented $OCH_3$, $R^3$ represented $NHCOCH_3$ and $R^4$ and $R^5$ represented $COCH_3$. The procedure was analogous to Example 1c.

Example 30 (diffusion transfer printing)

The dyestuff donor element was produced as follows: a 0.5% strength by weight solution of the dyestuff of Example 1 and a 0.5% strength by weight solution of a binder based on a styrene/acrylonitrile copolymer in tetrahydrofuran were applied, in a layer thickness of 100 μm in the moist state, to a 5 μm thin polyethylene terephthalate film, which had previously been provided with a layer of a vinylidene chloride/acrylonitrile copolymer (2.5 μm thick in the dry state). The layer formed was dried in vacuo. The reverse of the polyethylene terephthalate film was coated with a solution which contained 5% by weight of a styrene/acrylonitrile copolymer and 0.1% by weight of a 1% strength by weight solution of a polysiloxane/polyether copolymer (Tegoglide ® 410 from Th. Goldschmidt). This solution was applied in a thickness of 100 μm, and served to prevent the colour-donating element from sticking to the thermal print head. The dyestuff donor element thus obtained was employed in a Hitachi colour video printer VY-100 A for printing on commercially available recording material (Hitachi VY-S 100 A paper ink set).

An intensive cyan-coloured recording was obtained.

Analogous printing results with violet to blue-green recordings were obtained by using corresponding dyestuff donor elements which contained the products of Examples 2 to 29.

Example 31 (recording element which can be developed thermally)

A 0.5% strength by weight solution of the dyestuff obtained according to Example 4 in chloroform, which was intensely blue-coloured, was applied to a sheet of paper. After evaporation of the solvent, the blue colour disappeared and the coated paper was now coloured only pale beige. When the paper was written on with a heated glass rod, intense, stable violet-blue writing developed.

Analogous results were obtained when a polyethylene terephthalate film was employed instead of the sheet of paper and a thermal printer was used instead of the heated glass rod.

Analogous results were furthermore obtained when the recording element was prepared with solutions of the dyestuffs according to Examples 1 to 3 and 5 to 29.

Example 32 (recording element which can be developed photochemically)

A 0.5% strength by weight solution of the dyestuff obtained according to Example 9 in tetrahydrofuran, which is intensely blue-coloured, was applied to a polyethylene terephthalate film. After evaporation of the solvent, the blue colour had disappeared and the coating was only slightly beige-coloured. On exposure of the film with a flashlap, the coating became intense turquoise in colour. This colour remained unchanged for several days.

Analogous results were obtained when the dyestuffs according to Examples 1 to 8 and 10 to 29 were employed in a corresponding manner.

Analogous results were furthermore obtained when the film was exposed with a dyestuff laser (wavelength 460 μm, Coumarin 47 from Lambda Physik) ,instead of with a flash-lamp.

Example 33 (nonlinear optical element)

The dyestuff obtained according to Example 4 was irradiated in the form of a crystalline powder with laser light of wavelength 1064 nm .in an apparatus similar to that described by D. Lupo et al. in Adv Mater. 3, 54 (1991). During this procedure, emission of light of half the wavelength (=532 rim) was observed. When the irradiation was carried out with laser light of wavelength 820 nm, light having a wavelength of 410 nm was emitted.

Analogous results were obtained when the dyestuff obtained according to Example 23 was irradiated with laser light after it had been applied from a water surface to a glass plate in the form of a film.

Analogous results were likewise obtained when dyestuffs according to Examples 1 to 3, 5 to 22, 24 and 29 were employed.

Example 34 (photoreceptor element)

A photoreceptor element was produced in accordance with Example 11 of U.S. Pat. No. 4,471,041. Instead of the dyestuff used there, the dyestuff obtained according to Example 2 was employed.

A photoreceptor element which contained a photoconductive layer of the dyestuff obtained according to Example 2 in a polyester binder (1 μm thick) on an aluminum carrier, and on top of this a charge transportation layer comprising N,N'-diphenyl-N,N'-(3-methylphenyl)-1,1'-biphenyl-4,4'-diamine in a polycarbonate binder was obtained.

This element was charged to −760 V with a corona discharge. Exposure with light having an intensity of 150 mJ/m² at a wavelength of 600 nm led to a discharge of 60%.

Analogous results were obtained when dyestuffs obtained according to Examples 1 and 3 to 29 were employed.

Example 35 (dyeing of polyester)

0.1 g of the dyestuff obtained according to Example 8 was dissolved in dimethylformamide, and the solution was added to 300 ml of water, to which had been added 0.6 g of Avolan ® JS, as a carrier, 0.3 g of sodium dihydrogen phosphate and acetic acid, until a pH of 4.5 had been reached. 10 g of a woven polyester fabric of Trevira ® 2000 were added, and dyeing was carried out at 130° C. Thereafter, the woven fabric had a grey-blue colour shade.

Analogous results were obtained when the dyestuffs obtained according to Examples 1 to 7 and 9 to 29 were employed.

Example 36 (dyeing of plastics)

0.1 g of the dyestuff obtained according to Example 2 and 2 g of titanium dioxide were incorporated into 100 g of polystyrene and the mixture was injection moulded. An intensely blue-coloured injection moulding of plastic was obtained.

Analogous results were obtained when the dyestuffs obtained according to Examples 1 and 3 to 29 were employed.

What is claimed is:
1. Azinoneutromethines of the formula (I)

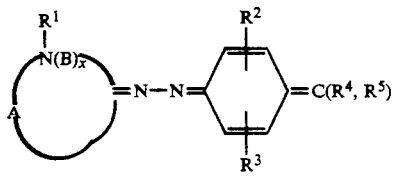

in which
$R^1$ represents $C_1$- to $C_{22}$-alkyl, $C_4$- to $C_{10}$-cycloalkyl, $C_7$- to $C_{14}$-aralkyl, $C_6$- to $C_{10}$-aryl, or a heterocyclic radical which is optionally bonded via $C_1$- to $C_2$-alkylene and contains 1 to 4 nitrogen, oxygen and/or sulphur atoms and 4 to 12 C atoms, it being possible for all these radicals optionally to be substituted, $R^2$ and $R^3$ independently of one another represent hydrogen, halogen, hydroxyl, cyano, $C_1$- to $C_8$-alkyl, $C_1$- to $C_8$-alkoxy, $C_4$- to $C_{10}$-cycloalkoxy, $C_7$- to $C_{14}$-aralkyloxy or $C_1$- to $C_{20}$-acylamino, $R^4$ and $R^5$ independently of one another represent cyano, $C_1$- to $C_8$-alkoxycarbonyl, $C_4$- to $C_7$-cycloalkoxycarbonyl, $C_6$- to $C_{10}$-aryloxycarbonyl, aminocarbonyl, mono-$C_1$- to $C_8$-alkylaminocarbonyl, di-$C_1$- to $C_8$-alkylaminocarbonyl, $C_6$- to $C_{10}$-arylaminocarbonyl, aminocarbonyl which is substituted by heterocyclic radicals which contain 5 to 7 atoms and contain N, S and/or O or phenyl which is substituted by cyano and/or nitro, or $R^4$ and $R^5$, together with the C atom in between, represent a ring which contains 5 or 6 atoms, optionally contains up to 2 nitrogen and/or oxygen atoms and is optionally substituted by cyano, halogen, $C_1$- to $C_4$-alkyl or $C_6$- to $C_{10}$-aryl, and A complements the ring in which it is located to form a 5- to 7-membered aromatic or quasiaromatic ring which is optionally benzo- or naphtho-fused, optionally contains a further nitrogen, oxygen or sulphur atom, and is optionally substituted by cyano, nitro, $C_1$- to $C_4$-alkyl, $C_7$- to $C_{12}$-aralkyl, $C_6$- to $C_{10}$-aryl, $C_1$- to $C_4$-alkoxy, a 5- to 6-membered ring which is optionally bonded via $C_1$- to $C_2$-alkylene and contains up to 2 N, S and/or O atoms, $C_1$- to $C_4$-alkylthio, $C_6$- to $C_{10}$-arylthio, amino, mono- or di-$C_1$- to $C_8$-alkylamino, $C_4$- to $C_8$-cycloalkyl-$C_1$- to $C_4$-alkylamino, $C_7$- to $C_{12}$-aryl-$C_1$- to $C_4$-alkylamino, mono- or di-$C_6$- to $C_{10}$-arylamino, pyrrolidino, piperidino, morpholino or $C_1$- to $C_6$-acylamino, represents $CR^B=CH$, where $R^B=$hydrogen or $C_1$- to $C_6$-alkyl, and x represents zero or 1.

2. Azinoneutromethines of claim 1, in which in formula (i), the radical
$R^2$ is in the ortho-position relative to the

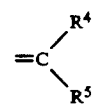

group and
$R^3$ is in the ortho-position relative to the $=N-N=$ group and in the para-position relative to $R^2$, and
$R^1$ represents $C_1$- to $C_{22}$- alkyl which is optionally branched and/or substituted by a total of up to three substituents from the group comprising $C_1$- to $C_4$-alkoxy, fluorine, chlorine, bromine, hydroxyl, cyano and aminocarbonyl, cyclopentyl, cyclohexyl, benzyl, phenethyl, phenyl which is optionally substituted by a total of up to 2 substituents from the group comprising $C_1$- to $C_4$-alkyl, $C_1$- to $C_4$-alkoxy, chlorine and cyano, or pyridylethyl, $R^2$ represents $C_1$- to $C_4$-alkyl, $C_1$- to $C_4$-alkoxy, chlorine, bromine, hydroxyl or cyano, $R^3$ represents hydrogen, $C_1$- to $C_4$-alkyl, $C_1$- to $C_4$-alkoxy, chlorine, bromine, hydroxyl, cyano, $C_1$- to $C_{20}$-alkanoylamino which is optionally substituted by up to nine fluorine atoms, or benzoylamino which is optionally substituted by a total of up to two substituents from the group comprising methyl, methoxy and chlorine, $R^4$ represents cyano, $C_1$- to $C_4$-alkoxycarbonyl, cyclopentoxycarbonyl, cyclohexoxycarbonyl, phenoxycarbonyl, aminocarbonyl, mono- or di-$C_1$- to $C_4$-alkylaminocarbonyl, anilinocarbonyl or nitrophenyl, $R^5$ represents cyano, A complements the ring in which it is located to form a pyrazole, imidazole, triazole, thiazole, thiadiazole, benzimidazole, benzothiazole, pyridine, pyrazine, pyrimidine or quinoline ring, it being possible for these rings optionally to be substituted by a total of up to two substituents from the group compressing chlorine, cyano, phenyl, $C_1$- to $C_4$-alkyl, $C_1$- to $C_4$-alkoxy, $C_1$- to $C_4$-alkylthio, phenylthio, di-$C_1$- to $C_4$-alkylamino, cyclohexyl-$C_1$- to $C_4$-alkylamino, benzyl-$C_1$- to $C_4$-alkylamino, phenylamino, phenyl-$C_1$- to $C_4$-alkylamino, pyrrolidino, piperidino or morpholino, it being possible for the substituents $C_1$- to $C_4$-alkoxy, $C_1$- to $C_4$-alkylthio, di-$C_1$- to $C_4$-alkylamino and cyclohexyl-$C_1$- to $C_4$-alkylamino in turn optionally to contain a total of up to two substituents from the group comprising chlorine, methoxy, ethoxy, hydroxyl and cyano, and for the substituents phenylamino and phenyl-$C_1$- to $C_4$-alkylamino in turn optionally to contain a total of up to two substituents from the group comprising methyl, methoxy, cyano and chlorine, and B represents CH=CH and x represents zero or 1.

3. Azinoneutromethines of claim 1, in which in (formula (I), the radical $R^2$ is in the ortho-position relative to the $$=C\begin{matrix}R^4\\R^5\end{matrix}$$

group and $R^3$ is in the ortho-position relative to the =N-N= group and in the para-position relative to $R^2$, and $R^1$ represents $C_1$- to $C_{16}$-alkyl which is optionally branched and/or substituted by a chlorine, cyano or methoxy group, or represents benzyl, $R^2$ represents methyl, ethyl, methoxy, ethoxy or chlorine, $R^3$ represents hydrogen, methyl, ethyl, methoxy, ethoxy, chlorine, cyano, formylamino, acetylamino, propionylamino, butyroylamino, octanoylamino, stearoylamino, trifluoroacetylamino, nonafluorobutyroylamino, benzoylamino, methylbenzoylamino or chlorobenzoylamino, $R^4$ represents cyano, methoxycarbonyl, ethoxycarbonyl, amidocarbonyl or 4-nitrophenyl, $R^5$ represents cyano, A complements the ring in which it is located to form one of the rings (II) to (VI)

(II) (III) (IV)

(V) (VI)

in which $R^1$ has the abovementioned meaning, $R^6$ represents hydrogen, methyl, ethyl, n-propyl, i-propyl, tert-butyl or phenyl and $R^7$ represents hydrogen, methyl, ethyl, chlorine or bromine, or $R^6$ and $R^7$ together represent —(CH$_2$)$_2$—, $R^8$ represents hydrogen, methyl, methoxy or chlorine, $R^9$ represents hydrogen, methyl, ethyl, phenyl, methylthio, phenylthio, anilino, 4-methylanilino, 4-methoxyanilino, N-methylanilino, dimethylamino, diethylamino, dipropylamino, dibutylamino, dihydroxyethylamino, dihydroxypropylamino, hydroxyethylcyclohexylamino, pyrrolidino, piperidino or morpholino and $R^{10}$ represents hydrogen, methyl, ethyl, phenyl or hydroxypropyl, and x represents zero.

4. Azinoneutromethines of claim 3, in which $R^2$ represents methoxy and $R^4$ represents cyano.

* * * * *

UNITED STATES PATENT AND TRADEMARK OFFICE
CERTIFICATE OF CORRECTION

PATENT NO : 5,328,994
DATED : July 12, 1994
INVENTOR(S): AZINONEUTROMETHINES It is certified that error appears in the above-identified patent and that said Letters Patent is hereby corrected as shown below:

Column 18, line 9,  before "represents" insert --B--

Column 18, line 54,  cancel "compressing" and substitute --comprising--

Column 20, line 27,  cancel "-(CH$_2$)$_2$- and substitute -- -(CH$_2$)$_4$- --

Signed and Sealed this

Twenty-ninth Day of June, 1999

*Attest:*

Q. TODD DICKINSON

*Attesting Officer*   *Acting Commissioner of Patents and Trademarks*